(12) United States Patent
Minai

(10) Patent No.: US 8,055,043 B2
(45) Date of Patent: Nov. 8, 2011

(54) IMAGING PROCESSOR, BODY-INTRODUCABLE APPARATUS, MEDICAL SYSTEM AND IMAGE PROCESSING METHOD

(75) Inventor: Tetsuo Minai, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 78 days.

(21) Appl. No.: 12/761,857

(22) Filed: Apr. 16, 2010

(65) Prior Publication Data

US 2010/0266202 A1   Oct. 21, 2010

Related U.S. Application Data

(63) Continuation of application No. PCT/JP2009/068192, filed on Oct. 22, 2009.

(30) Foreign Application Priority Data

Oct. 27, 2008   (JP) ................. 2008-275859

(51) Int. Cl.
*G06K 9/00* (2006.01)
(52) U.S. Cl. ..................................... 382/128
(58) Field of Classification Search .................. 382/128, 382/131, 132
See application file for complete search history.

(56) References Cited

U.S. PATENT DOCUMENTS

2003/0071894 A1   4/2003   Higuchi et al.

FOREIGN PATENT DOCUMENTS

| JP | 4-340888 | 11/1992 |
|---|---|---|
| JP | 5-228108 | 9/1993 |
| JP | 2000-330037 | 11/2000 |
| JP | 2001-352555 | 12/2001 |
| JP | 2003-93342 | 4/2003 |
| JP | 2005-74034 | 3/2005 |
| JP | 2005-192880 | 7/2005 |
| JP | 2006-297093 | 11/2006 |
| JP | 2006-341078 | 12/2006 |
| JP | 2007-319442 | 12/2007 |

OTHER PUBLICATIONS

Japanese Official Action dated Jul. 6, 2010 together with an English language translation.
International Search Report dated Jan. 19, 2010.

*Primary Examiner* — Claire X Wang
(74) *Attorney, Agent, or Firm* — Scully, Scott, Murphy & Presser, P.C.

(57) ABSTRACT

An imaging processor includes an amplifier that increases luminance indicated by green and blue image data on the basis of luminance indicated by red image data out of a plurality of pieces of image data in respective wavelength components, which are pieces of image data representing the same area.

7 Claims, 14 Drawing Sheets

IMAGING PROCESSOR, BODY-INTRODUCABLE APPARATUS, MEDICAL SYSTEM AND IMAGE PROCESSING METHOD

CROSS-REFERENCE TO RELATED APPLICATIONS

This application is a continuation of PCT international application Ser. No. PCT/JP2009/068192 filed on Oct. 22, 2009 which designates the United States, incorporated herein by reference.

BACKGROUND OF THE INVENTION

1. Field of the Invention

The present invention relates to an imaging processor, a body-introducable apparatus, a medical system and an image processing method. Particularly, the present invention relates to an imaging processor that is introduced into a subject, such as a human, an animal, a plant or an object, and obtains in-vivo images of the subject, a body-introducable apparatus, a medical system and an image processing method.

2. Description of the Related Art

Conventionally, there are capsule endoscopic systems that generate multi-spectral images in an arbitrary wavelength band from image data that is obtained by capturing in-vivo images of a subject while illuminating the inside of the subject using a light source that outputs white light (for example, see Japanese Laid-open Patent Publication No. 2007-319442).

SUMMARY OF THE INVENTION

An imaging processor according to an aspect of the present invention includes an amplifier that increases luminance indicated by green and blue image data on the basis of luminance indicated by red image data out of a plurality of pieces of image data in respective wavelength components, which are pieces of image data representing the same area.

A body-introducable apparatus according to an aspect of the present invention is a body-introducable apparatus that is introduced into a subject. The body-introducable apparatus includes an imaging processor that includes an amplifier that increases luminance indicated by green and blue image data on the basis of luminance indicated by red image data out of a plurality of pieces of image data in respective wavelength components, which are pieces of image data representing the same area; a light source that outputs white light; and an imaging unit that acquires the pieces of image data in the respective wavelength components, which are pieces of image data representing the same area, by capturing in-vivo images of the subject of which inside is illuminated with the white light.

A medical system according to an aspect of the present invention is a medical system that includes a body-introducable apparatus that is introduced into a subject; and an external device that is arranged outside the subject. The body-introducable apparatus includes an imaging processor that includes an amplifier that increases luminance indicated by green and blue image data on the basis of luminance indicated by red image data out of a plurality of pieces of image data in respective wavelength components, which are pieces of image data representing the same area; a light source that outputs white light; an imaging unit that acquires the pieces of image data in the respective wavelength components, which are pieces of image data representing the same area, by capturing in-vivo images of the subject of which inside is illuminated with the white light; and a transmitter that transmits the green and blue image data that is amplified by the amplifier to the external device. The external device includes a receiver that receives the amplified green and blue image data that is transmitted from the transmitter.

A medical system according to another aspect of the present invention includes a body-introducable apparatus that is introduced into a subject; and an external device that is arranged outside the subject. The body-introducable apparatus includes a light source that outputs white light; an imaging unit that acquires a plurality of pieces of image data in respective wavelength components, which are pieces of image data representing the same area, by capturing in-vivo images of the subject of which inside is illuminated with the white light; and a transmitter that transmits the pieces of image data in the respective wavelength components, which are pieces of image data representing the same area, to the external device. The external device includes a receiver that receives the pieces of image data in the respective wavelength components, which are pieces of image data that represent the same area and transmitted from the transmitter; and an imaging processor that includes an amplifier that increases luminance indicated by green and blue image data on the basis of luminance indicated by red image data out of the pieces of image data in the respective wavelength components, which are pieces of image data that represent the same area.

An image processing method according to an aspect of the present invention includes an amplifying step of increasing luminance indicated by green and blue image data on the basis of luminance indicated by red image data out of a plurality of pieces of image data in respective wavelength components, which are pieces of image data representing the same area.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 1:
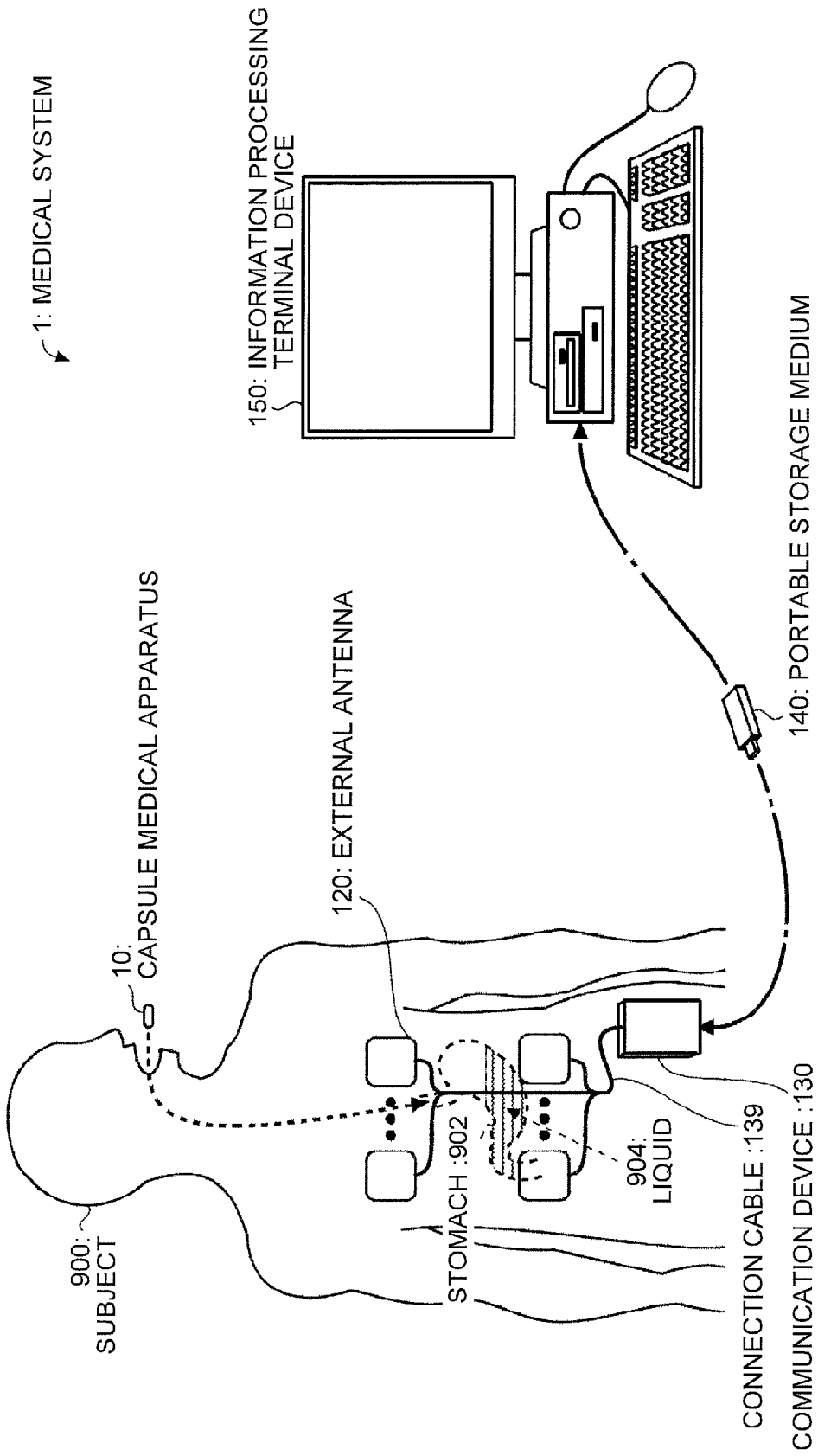
FIG. 1 is a schematic diagram of a schematic configuration of a medical system according to a first embodiment or a second embodiment of the present invention.

Best modes for carrying out the invention will be explained in detail below with reference to the drawings. In the following explanations, each drawing only schematically represents the shape, size and positional relationship such that the contents of the present invention are understood; therefore, the present invention is not limited to the shape, size and positional relationship that are exemplified in the drawings. In the drawings, hatching is partly omitted in the cross sectional view to simplify the configuration. The numeric values exemplified below are only preferable examples of the present invention and the present invention is not limited to the exemplified numeric values.

First Embodiment

First, a medical system 1 according to a first embodiment of the present invention will be explained in detail with reference to the drawings. In the first embodiment, a case is taken as an example where a capsule medical apparatus 10 is used as a body-introducable apparatus that floats in a liquid 904, which is stored in a stomach 902 of a subject 900, to capture images of the inner wall of the stomach 902. However, the present invention is not limited to this case. The capsule medical apparatus 10 according to the first embodiment may be used as a body-introducable apparatus that captures in-vivo images of the subject 900 while moving from the esophagus to the anus. The internal organ in which the liquid 904 is stored is not limited to the stomach 902. Various organs, such as the small intestine and the large intestine, may serve as such internal organs. It is preferable that a liquid, such as normal saline or water that has no adverse effects on the subject 900 and the capsule medical apparatus 10 be used.

In the first embodiment, a case is exemplified where the inside of the subject 900 is illuminated with white light, which contains wavelength components of red (R), green (G), and blue (B), and, in this state, in-vivo images of the subject 900 are captured to obtain image data in each of the wavelength components of red (R), green (G), and blue (B). However, the present invention is not limited to this. It suffices that image data in at least two wavelength components be obtained by illuminating the inside of the subject 900 with light that contains at least two wavelength components out of red (R), green (G), and blue (B), and, in this state, in-vivo images of the subject 900 be captured.

In the following explanations, light (including white light) that contains wavelength components of red (R), green (G), and blue (B) is referred to as normal light, and light that consists of only any one of these wavelength components is referred to as special light. Image data that contains wavelength components of red (R), green (G), and blue (B) is referred to as a normal light image and an image consisting of one or two of those wavelength components is referred to as a special light image. In the following explanations, operations for generating a normal light image are referred to as normal light observation and operations for generating a special light image are referred to as special light observation. The first embodiment is an example where both normal light observation and special light observation are performed in a manner that a normal light image and a special light image are generated from image data, which is obtained by capturing images by using illumination with normal light.

FIG. 1 is a schematic diagram of a schematic configuration of the medical system 1 according to the first embodiment. As illustrated in FIG. 1, the medical system 1 includes the capsule medical apparatus 10 that is introduced perorally to the subject 900 and floats in the liquid 904 that is stored in the stomach 902, and also includes a communication device 130 that communicates image data and control instructions with the capsule medical apparatus 10 by performing radio communications with the capsule medical apparatus 10.

The communication device 130 is configured such that a portable storage medium 140, such as a flash Memory® or a Smartcard®, is detachable from the communication device 130. The portable storage medium 140 stores, for example, image data on in-vivo images that are captured by the capsule medical apparatus 10. A user can visually check in-vivo images of the subject, which are captured by the capsule medical apparatus 10, in a manner that the portable storage medium 140 is connected to an information processing terminal device 150, such as a personal computer or a server, the information processing terminal device 150 reads image data, which is stored in the portable storage medium 140, and displays the in-vivo images of the subject on the display unit of the information processing terminal device 150. In the following explanations, an external antenna 120, the communication device 130, and the information processing terminal device 150 are referred to as external devices.

The communication device 130 is arranged outside the subject 900. One or more external antennae 120 are connected to the communication device 130 via a connection cable 139, such as a co-axial cable. Each of the external antennae 120 is arranged outside the subject 900 and near the capsule medical apparatus 10. The communication device 130 communicates data with the capsule medical apparatus 10 via the external antennae 120.

Figure 2:
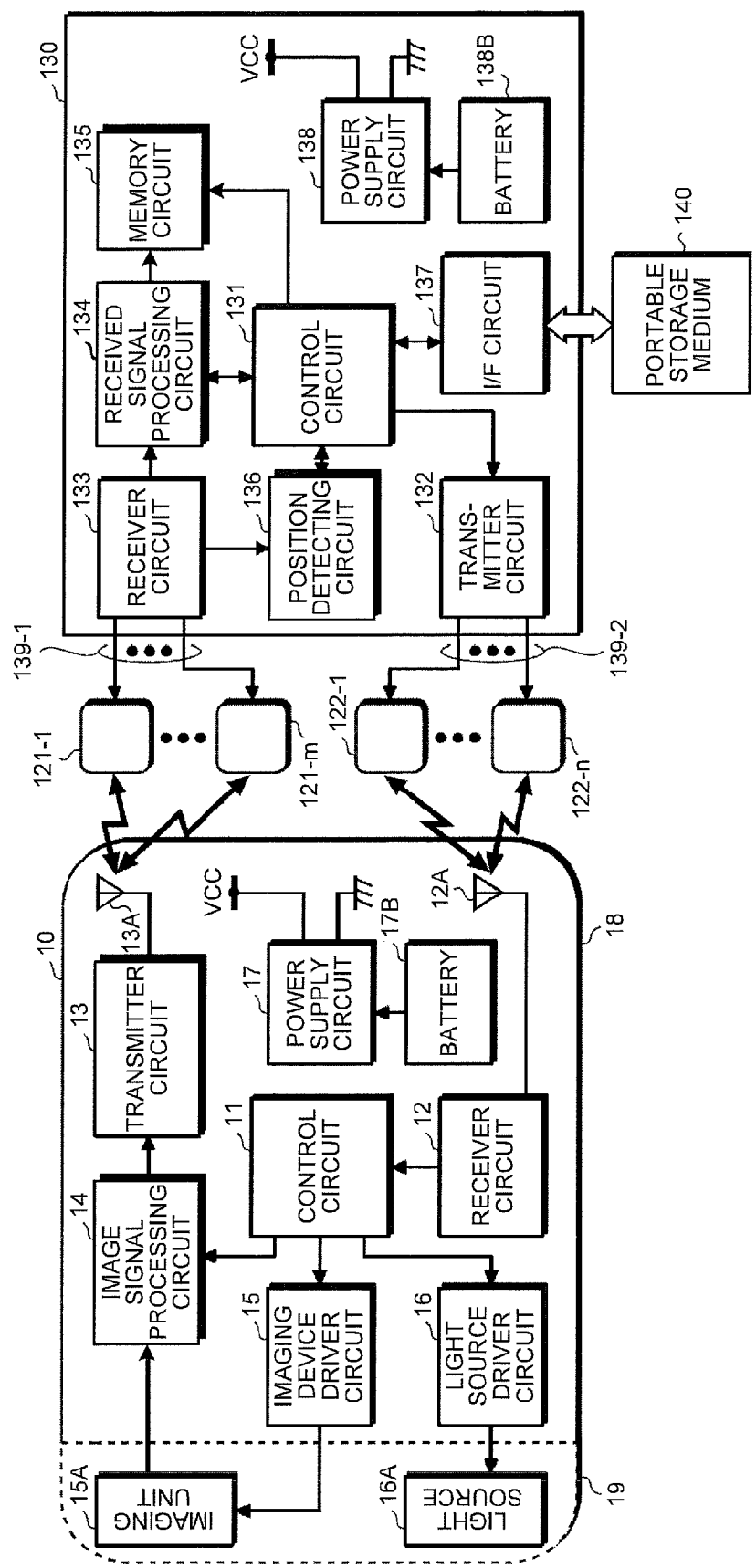
FIG. 2 is a block diagram of a schematic configuration of devices that constitutes the medical system according to the first embodiment or the second embodiment of the present invention.
Figure 3:
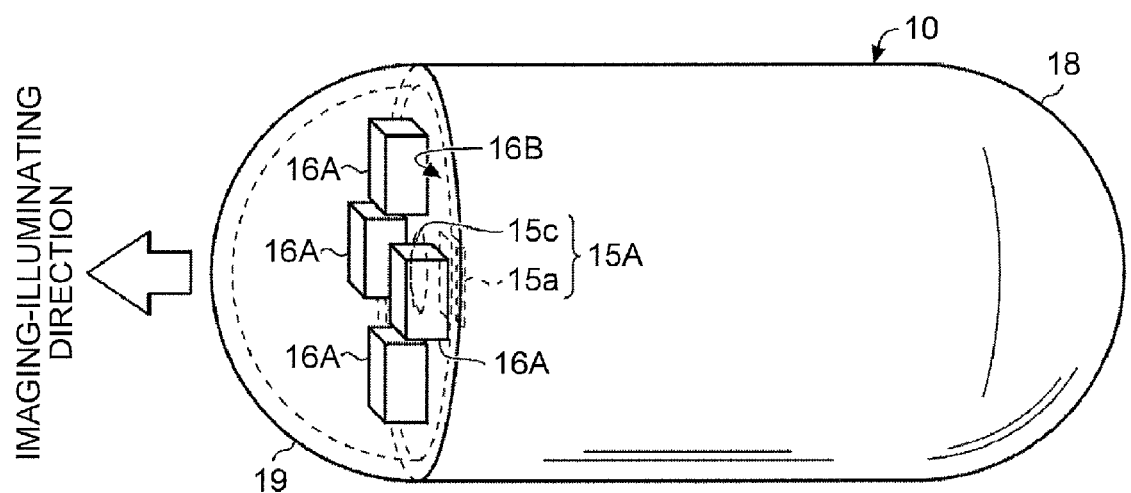
FIG. 3 is a perspective view of a schematic configuration of a capsule medical apparatus according to the first embodiment or the second embodiment of the present invention.

The medical system 1 according to the first embodiment will be explained in detail below with reference to FIGS. 2 and 3. FIG. 2 is a block diagram of a schematic configuration of each device that constitutes the medical system 1 according to the first embodiment. FIG. 3 is a perspective view of a schematic configuration of the capsule medical apparatus 10 according to the first embodiment.

Capsule Medical Apparatus

An example of the capsule medical apparatus 10 according to the first embodiment will be explained in detail with reference to FIG. 2. As illustrated in FIG. 2, the capsule medical apparatus 10 that is introduced into the subject 900 includes an imaging unit 15A and an imaging device driver circuit 15 for capturing in-vivo images of the subject 900; a light source 16A and a light source driver circuit 16 for illuminating the inside of the subject 900 when images are captured; an image signal processing circuit 14 that performs predetermined processes on image signals, which are generated by the imaging unit 15A, to generate image data; a transmitter circuit 13 and a transmitting antenna 13A for outputting the image data, which is generated by the image signal processing circuit 14, to the outside as radio signals; a receiver circuit 12 and a receiving antenna 12A for receiving control signals, which are transmitted as radio signals from the communication device 130 arranged outside the subject 900; a control circuit 11 that performs drive control on each circuit in the capsule medical apparatus 10; and a battery 17B and a power supply circuit 17 for supplying electric power to each circuit in the capsule medical apparatus 10.

According to, for example, control instructions, which are received from the communication device 130 via the receiver circuit 12, and programs and control parameters, which are previously stored in memories of the control circuit 11, the control circuit 11 performs drive control on the imaging device driver circuit 15, the light source driver circuit 16, and the image signal processing circuit 14 that causes them to perform the image capturing operations regularly (for example, two frames in a second) and to transmit image data obtained using the image capturing operations to the communication device 130 via the transmitter circuit 13.

The capsule medical apparatus 10 may include a sensor device (not illustrated) and a sensor device driver circuit that performs drive control on the sensor device. The sensor device includes, for example, a thermometer, a pressure meter, and a pH meter. The sensor device appropriately acquires the temperature, the pressure, and the pH inside the subject 900 as in-vivo information. The sensor device control circuit acquires in-vivo information by driving the sensor device under the control of the control circuit 11 and inputs the in-vivo information to the transmitter circuit 13. The transmitter circuit 13 transmits the input in-vivo information to the communication device 130.

As illustrated in FIG. 2, each circuit in the capsule medical apparatus 10 is housed in a capsule-shaped casing that includes a casing 18 and a cap 19. As illustrated in FIG. 3, the casing 18 is approximately cylindrical or ellipsoidal with one end that is semi-spherical and dome shaped and the other end that is open. The cap 19 is semi-spherical and fitted to the opening of the casing 18 so the casing 18 is sealed. The capsule-shaped casing that includes the casing 18 and the cap 19 is sized such that it can be swallowed by the subject 900. In the first embodiment, at least the cap 19 is formed of a transparent material. The light source 16A is mounted on a circuit board 16B that is arranged on the side of the cap 19 inside the capsule-shaped casing (18, 19). Similarly, the imaging unit 15A is mounted on a circuit board (not illustrated) that is arranged on the side of the cap 19 inside the capsule casing (18, 19). The surfaces of the circuit boards on which devices are mounted face the cap 19. Therefore, the imaging and illuminating directions of the respective imaging unit 15A and the light source 16A are toward the subject 900 via the transparent cap 19, as illustrated in FIG. 3. An objective lens 15c is arranged on the light receiving surface of the imaging unit 15A. The cap 19 serves as a lens for adjusting distribution of light that is output from the light source 16A and/or of light that is incident on an imaging device 15a via the objective lens 15c and also serves as a lens for increasing the angle of the light source 16A and the imaging unit 15A for imaging and illuminating areas.

Communication Device

An example of the communication device 130 according to the first embodiment will be explained in detail with reference to FIG. 2. As illustrated in FIG. 2, the communication device 130 that is arranged on the outer surface of the subject 900 (for example the surface of the subject 900 or cloths that the subject 900 wears) includes a control circuit 131 that performs drive control on each circuit in the communication device 130; a receiver circuit 133 and m (where m is 1 or larger) external antennae 121-1 to 121-m, which are connected to the receiver circuit 133 via connection cables 139-1, for receiving image data that is transmitted as radio signals from the capsule medical apparatus 10; a received signal processing circuit 134 that performs predetermined processes on the received image signals; a memory circuit 135 that stores image data obtained by performing the predetermine processes; an interface circuit 137 from which the portable storage medium 140 is detachable; a transmitter circuit 132 and n (where n is 1 or larger) external antennae 122-1 to 122-n, which are connected to the transmitter circuit 132 via connection cables 139-2, for transmitting control instructions for the capsule medical apparatus 10, which are instructions generated by the control circuit 131, as radio signals to the capsule medical apparatus 10; and a battery 138B and a power supply circuit 138 for supplying electric power to each circuit in the communication device 130.

The image data that is obtained through processing by the received signal processing circuit 134 may be stored in the memory circuit 135 under the control of the control circuit 131 or stored in the portable storage medium 140 that is connected to the interface circuit 137. The control circuit 131 may transmit the image data, which is obtained through processing by the received signal processing circuit 134, to an externally-connected display device via a graphic board (not illustrated) or displayed on a display unit with which the communication device 130 is provided.

The communication device 130 may be further provided with an operating unit for an operator to input various operations, such as imaging capturing instructions, or may be configured to perform wireless or wired communications with another device that is provided with such an operating unit.

The communication device 130 may be further provided with a position detecting circuit 136 that detects the position of the capsule medical apparatus 10 in the subject 900 on the basis of the radio wave field intensity of the radio signals, which are received by the receiver circuit 133, and the position of the external antenna 120, which is fixed on the outer surface of the subject 900. The position of the capsule medical apparatus 10, which is detected by the position detecting circuit 136, is input to the control circuit 131 and stored together with the image data, which is received from the capsule medical apparatus 10 in synchronization with the detecting of the capsule's position, in the memory circuit 135 or the portable storage medium 140.

Normal light observation and special light observation

A configuration and operations for generating normal light images and special light images from image data that is acquired using the capsule medical apparatus 10 according to the first embodiment will be explained in detail with reference to the drawings.

As described above, in the first embodiment, the inside of the subject 900 is illuminated with normal light containing wavelength components of red (R), green (G), and blue (B) and, in this state, in-vivo images of the subject 900 are captured to obtain image data in each of the wavelength components of red (R), green (G), and blue (B). The image data consists of a plurality of pieces of image data in the respective wavelength components for the same area.

In the first embodiment, normal light images are generated using the image data in the wavelength components of red (R), green (G), and blue (B) (normal light observation) and special light images are generated using the image data in the wavelength components of green (G) and blue (B) out of red (R), green (G), and blue (B) (special light observation). However, special light images are not limited to this. Special light images that are generated using special light observation may be images only of the wavelength component of green (G) or images only of the wavelength component of blue (B).

Figure 4:
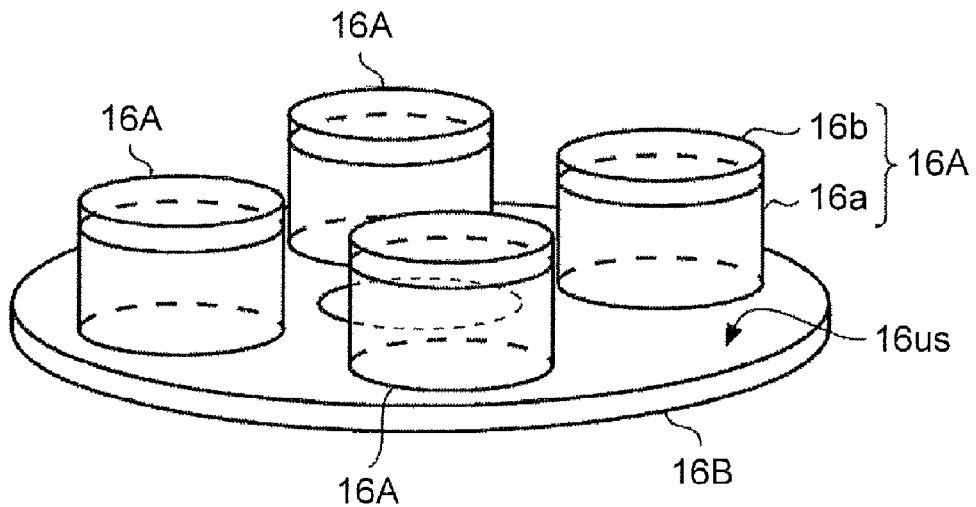
FIG. 4 is a perspective view of a schematic configuration of a light source according to the first embodiment or the second embodiment of the present invention.

FIG. 4 is a perspective view of a schematic configuration of the light source 16A according to the first embodiment. To facilitate an explanation, FIG. 4 omits configurations other than those of the light source 16A of the capsule medical apparatus 10 and the circuit board 16B, on which the light source 16A is mounted.

As illustrated in FIG. 4, in the first embodiment, four light sources 16A are mounted on a surface 16us of the circuit board 16B, which is the surface on which devices are mounted. Each light source 16A includes a light emitting device 16a that is driven by a voltage, which is applied from the light source driver circuit 16, and outputs light. The light source driver circuit 16 is mounted on the circuit board 16B and electrically connected with the light source 16A. The surface 16us on which devices are amounted is arranged such that it faces the cap 19.

A white LED (light emitting diode) that outputs, for example, white light (normal light) or an LED that outputs, for example, light in a predetermined wavelength band around, for example, 415 nm (special light) can be used for the light emitting device 16a. Note that, if an LED that outputs light in the predetermined wavelength band for example, around 415 nm (special light) is used for the light emitting device 16a, a wavelength converter 16b is provided that converts the wavelength of the special light that is output from the light emitting device 16a and outputs normal light that contains blue (B) light, green (G) light, and red (R) light. In this case, the wavelength converter 16b and the light emitting device 16a are collectively referred to as the light source 16A in the explanations. The red (R) light is, for example, light in a wavelength band around 680 nm, the green (G) light is, for example, light in a wavelength band around 540 nm, and the blue (B) light is, for example, light in a wavelength band around 415 nm. More specifically, light in the wavelength band around 415 nm is light of a wavelength between 380 nm to 460 nm and light in the wavelength band around 540 nm is light of a wavelength between 500 nm and 580 nm.

Figure 5:
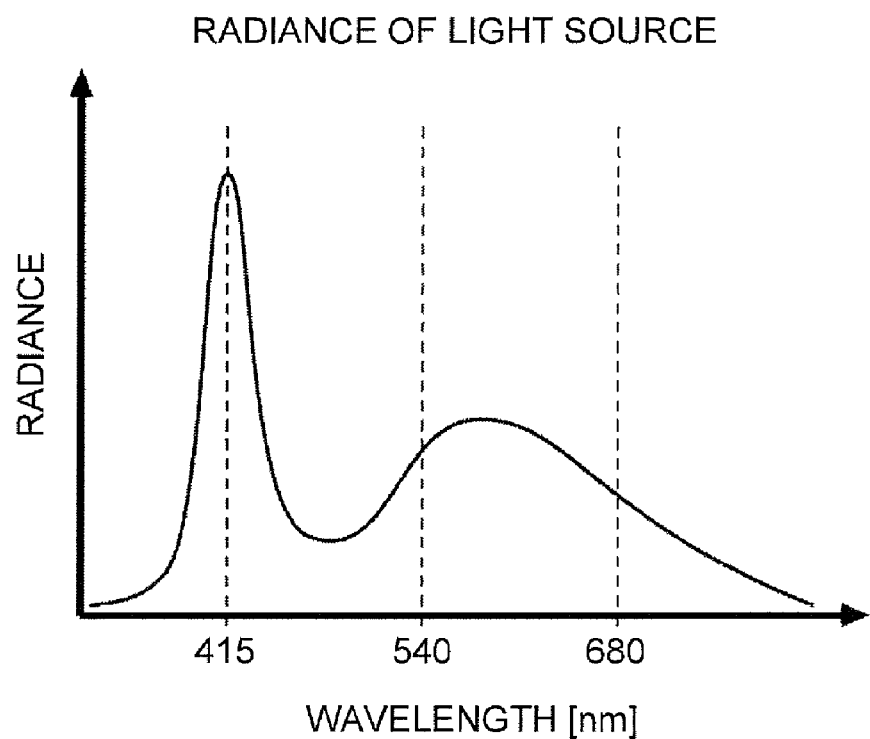
FIG. 5 is a graph representing the radiance of the light source that is used in the first embodiment or the second embodiment of the present invention.

FIG. 5 represents the radiance of the light source 16A that is used in the first embodiment. As represented in FIG. 5, in the first embodiment, the light source 16A outputs normal light that contains light in the wavelength band around 415 nm (blue (B) component), light in the wavelength band around 540 nm (green (G) component), and light in the wavelength band around 680 nm (red (R) component).

In the first embodiment, the light source 16A is configured such that the orientations the respective light wavelength components, which are output from each of the light sources 16A, are the same or approximately the same. Furthermore, in the first embodiment, the light sources 16A are laid out such that the orientations of the light wavelength components, which are output from the respective light sources 16A arranged on the circuit board 16B, are the same or approximately the same. For example, the orientation of special light of the red (R) color component, special light of the green (G) color component, and special light of the blue (B) color component out of the normal light, which is output from the light sources 16A, coincide. In addition, provided that the light sources 16A are one light source, the orientation of the special light of the red (R) color component, the special light of the green (G) color component, and the special light of the blue (B) color component all coincide. By achieving the same orientation of the special light color components, images without color unevenness can be captured. As a method of achieving the same orientation of light, various methods can be used, for example, providing the light extraction surface of the light source 16A with a film that diffuses light or arranging the light sources 16A symmetrically around the imaging device.

Figure 6:
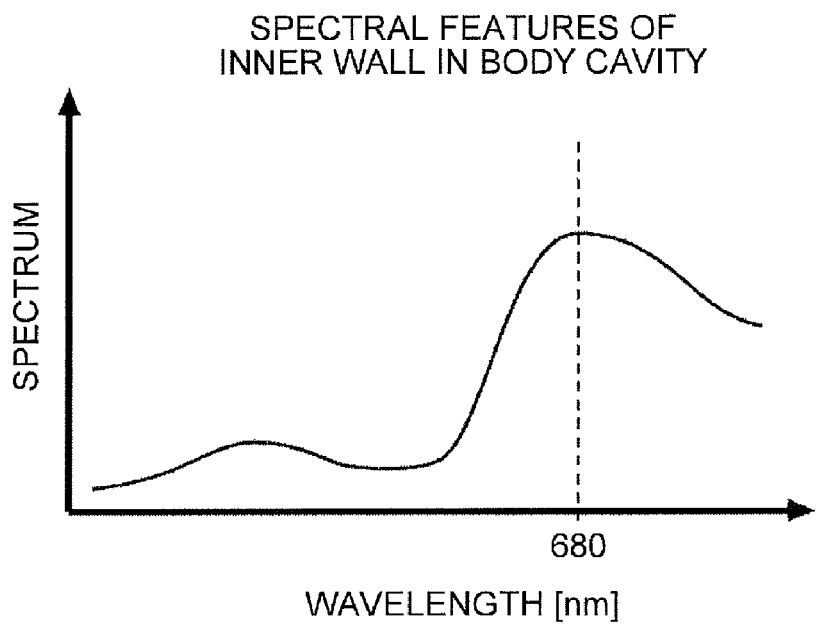
FIG. 6 is a graph of the spectral features of the inner wall in the body cavity in a case where the subject is a human or an animal.

When the subject 900 is, for example, a human or an animal, the spectral features with respect to red (R) are stronger than those with respect to green (G) and blue (B) in the case where the inner wall of the body cavity (the imaging object) is illuminated. In other words, as represented in FIG. 6, the spectral features of the inner wall of the body cavity of the subject 900 form a curve that has a peak around 680 nm. FIG. 6 is a graph of the spectral features of the inner wall in the body cavity in the case where the subject is a human or an animal.

Figure 7:
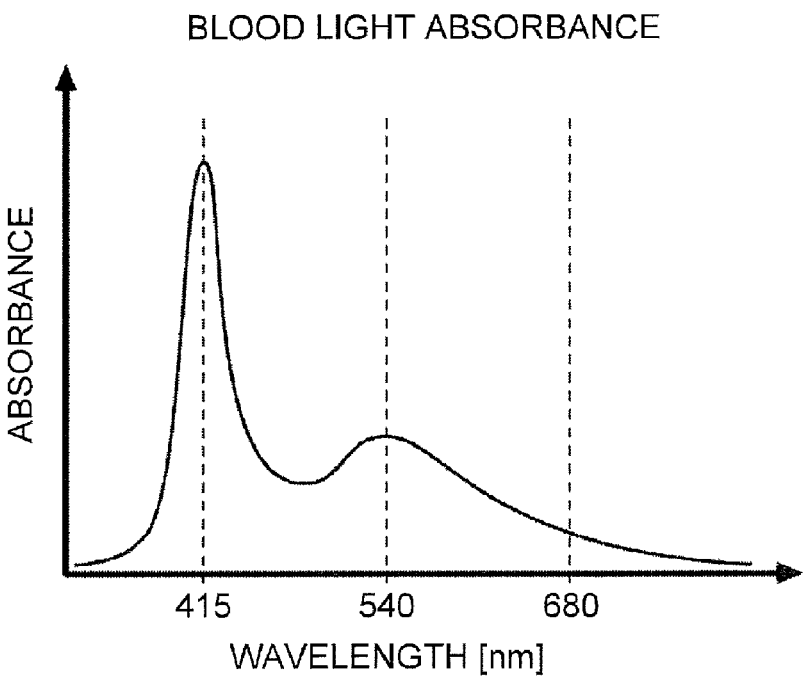
FIG. 7 is a graph of the light absorbance by blood of a human or an animal.

In contrast, as represented in FIG. 7, the blood of a human or an animal significantly absorbs light in the wavelength band around 415 nm and light in the wavelength band around 540 nm compared to light in the wavelength band around 680 nm. Therefore, if the subject 900 is a human or an animal, the shape of blood vessels, in which blood concentrates, can be obtained by receiving the reflected light in the wavelength band around 415 nm and the reflected light in the wavelength band around 540 nm. FIG. 7 is a graph representing the light absorbance by the blood of a human or an animal.

Figure 8:
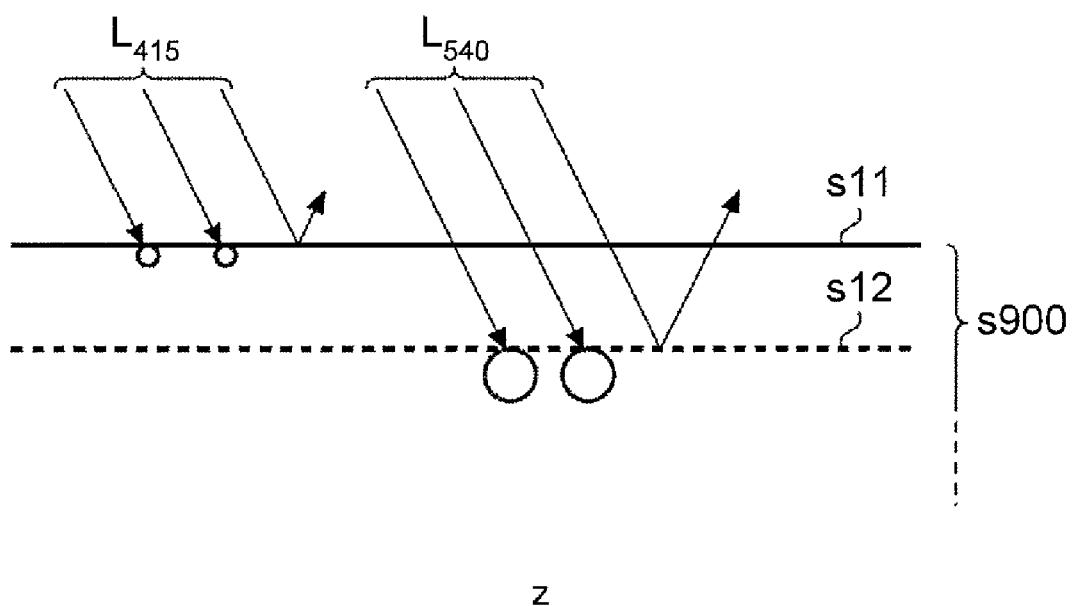
FIG. 8 is a schematic diagram for explaining how light in a wavelength band of about 415 nm and light in a wavelength band of 540 nm reflects off the inner wall of the subject.

Generally, longer wavelengths have greater the transmittance with respect to objects is. In other words, as illustrated in FIG. 8, light $L_{415}$ in the wavelength band around 415 nm is absorbed by blood vessels near a surface s11 of the inner wall s900 of the subject 900. The unabsorbed light $L_{415}$ is reflected near the surface s11 of the inner wall s900. Thus, by observing the light $L_{415}$ (special light) in the wavelength band around 415 nm using spectroscopy, the shape of the blood vessels near the surface s11 of the inner wall s900 of the subject 900 can be obtained. In contrast, light $L_{540}$ in the wavelength band around 540 nm is absorbed by blood vessels near a relatively deep layer portion S12 in the inner wall s900, as illustrated in FIG. 8. The unabsorbed light $L_{540}$ is reflected by the relatively deep layer portion S12 in the inner wall s900 of the subject 900. By observing the light $L_{540}$ in the wavelength band around 540 nm using spectroscopy, the shape of blood vessels in the relatively deep layer portion S12 in the inner wall s900 of the subject 900 can be obtained. FIG. 8 is a schematic diagram explaining how light in the wavelength band around 415 nm and light in the wavelength band around 540 nm are reflected by the inner wall s900 of the subject 900.

By superimposing one of a special light image, which is obtained by receiving the light $L_{415}$ (special light) in the wavelength band around 415 nm, and a special light image, which is obtained by receiving the light $L_{540}$ (special light) in the wavelength band around 540 nm, on the other, special light observation for imaging a three-dimensional shape of the vessels in the subject 900 can be performed. By superimposing a normal light image, which is obtained through normal light observation, on the superimposed special light image, an image can be obtained in which the shape of the inner wall and a three-dimensional shape of the blood vessels thereof are produced.

Figure 9:
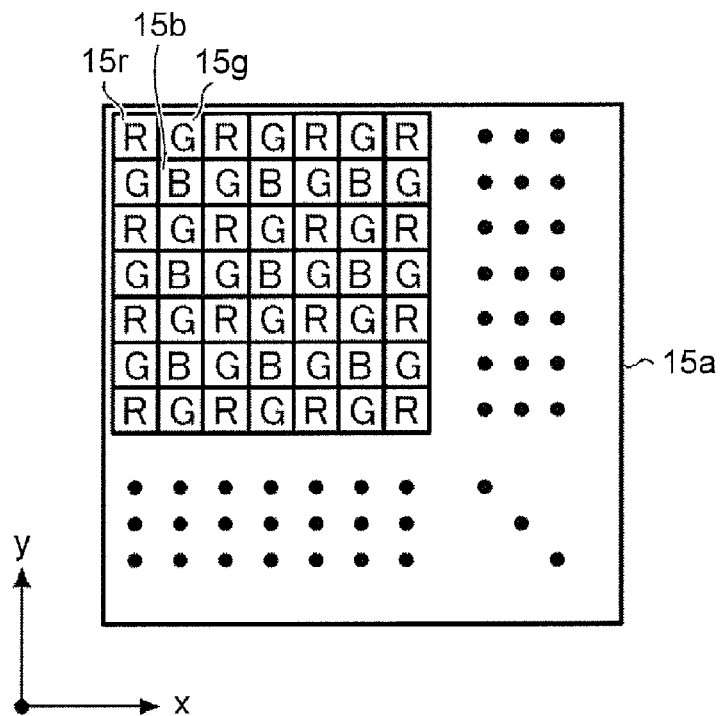
FIG. 9 is a layout view of a schematic configuration of an imaging device according to the first embodiment or the second embodiment of the present invention.
Figure 10:
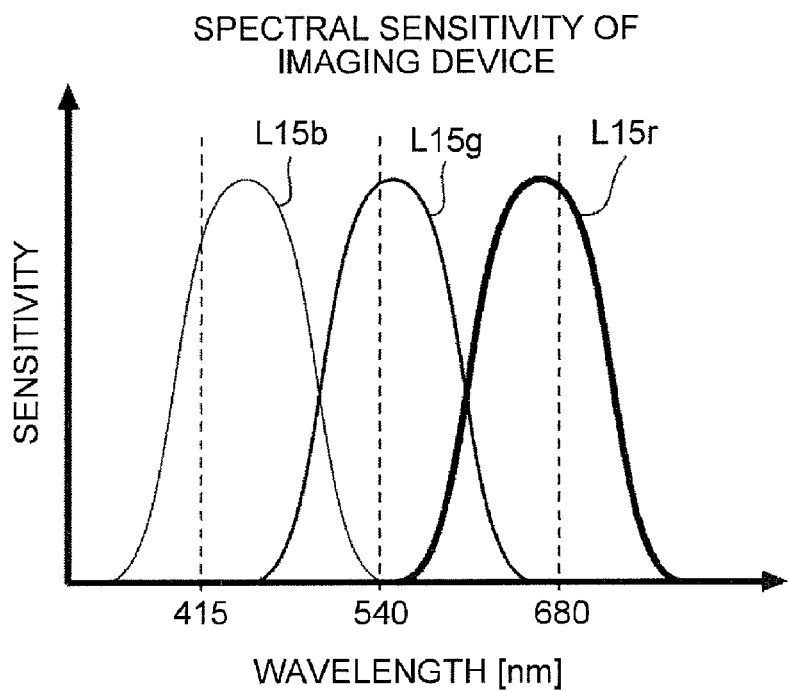
FIG. 10 is a graph of the spectral sensitivity of each device in the imaging device according to the first embodiment or the second embodiment of the present invention.

In the first embodiment, in-vivo images of the subject 900 are captured using the imaging device 15a in which, as illustrated in FIGS. 9 and 10, light receiving devices 15b that receive light of a wavelength component around 415 nm (blue (B) component), light receiving devices 15g that receive light of a wavelength component around 540 nm (green (G) component), and light receiving devices 15r that receive light of a wavelength component (red (R) component) around 680 nm are in a regular, two-dimensional arrangement. Accordingly, image data consisting of the wavelength component around 415 nm (blue (B) component) (hereinafter, "B data"), image data consisting of the wavelength component around 540 nm (green (G) component) (hereinafter, "B data"), image data consisting of the wavelength component around 680 nm (red (R) component) (hereinafter, "R data") can be generated.

FIG. 9 is a layout view of a schematic configuration of the imaging device 15a according to the first embodiment. FIG. 10 is a graph of the spectral sensitivity of each device in the imaging device 15a. The line L15b represented in FIG. 10 denotes the spectral sensitivity of the light receiving device 15b, the line L15g denotes the spectral sensitivity of the light receiving device 15g, and the line L15r denotes the spectral sensitivity of the light receiving device 15r.

In the following explanation, an area in the subject 900 of which images are captured by the light receiving devices 15r, 15g, and 15b that are arranged regularly in a line (horizontally in FIG. 9) is referred to as a unit area. In other words, in the example represented in FIG. 9, the total area, of which images are captured by the three light receiving devices, i.e., the light receiving device 15g, the light receiving device 15r, and the light receiving device 15b, is the unit area. By sequentially reading the imaging device 15a in the imaging unit 15A line by line, the imaging device driver circuit 15 obtains one piece of image data that contains R data, G data, and B data. The area defined as a unit area is not limited to an area of which an image is captured in one pixel. Various modifications can be made for the area.

As described above, the spectral features of the inner wall in the body cavity in the case where the subject 900 is a human or an animal has a peak near 680 nm. Therefore, the signal intensity (or the pixel value) of the G data, which is obtained by the light receiving device 15g, and the signal intensity of the B data, which is obtained by the light receiving device 15b, are significantly smaller than that of the signal intensity of the R data, which is obtained by the light receiving device 15r. For this reason, when normal light observation and special light observation are simultaneously performed, the S/N ratio of the G data and the B data becomes extremely small. This makes it difficult to obtain clear blood vessel images through special light observation.

In the first embodiment, by increasing the luminance indicated by image data in another wavelength component on the basis of the luminance indicated by image data in a predetermined wavelength component, the contrast between the blood vessels and other portions in the G data and the contrast between the blood vessels and other portions in the B data can be adjusted. This leads to special light observation through which clear special light images can be obtained.

In the first embodiment, the signal intensity of the R data, i.e., the luminance indicated by the R data, is used as a parameter for determining the increasing rate at which the luminance indicated by the G data and the luminance indicated by the G data are increased. As described above, the R data has the highest signal intensity among the red (R), green (G), and blue (B) components. Therefore, by amplifying the G data and the B data using the R data, the dynamic range of the G data and the B data can be substantially increased. Accordingly, clear images with high contrast can be generated.

In addition, as described above, the R data particularly contains the shape of the inner wall of the body cavity (the imaging object) in a case where the subject 900 is a human or an animal. Therefore, by amplifying the G data and the B data using the R data with respect to each corresponding unit area between the R data, the G data, and the B data, the signal intensity (or pixel value) can be accurately amplified according to the shape of the inner wall of the body cavity. Accordingly, the contrast can be adjusted accurately while reducing noises and special light images can be produced in which a favorable three-dimensional shape of the blood vessels is produced.

Figure 11:
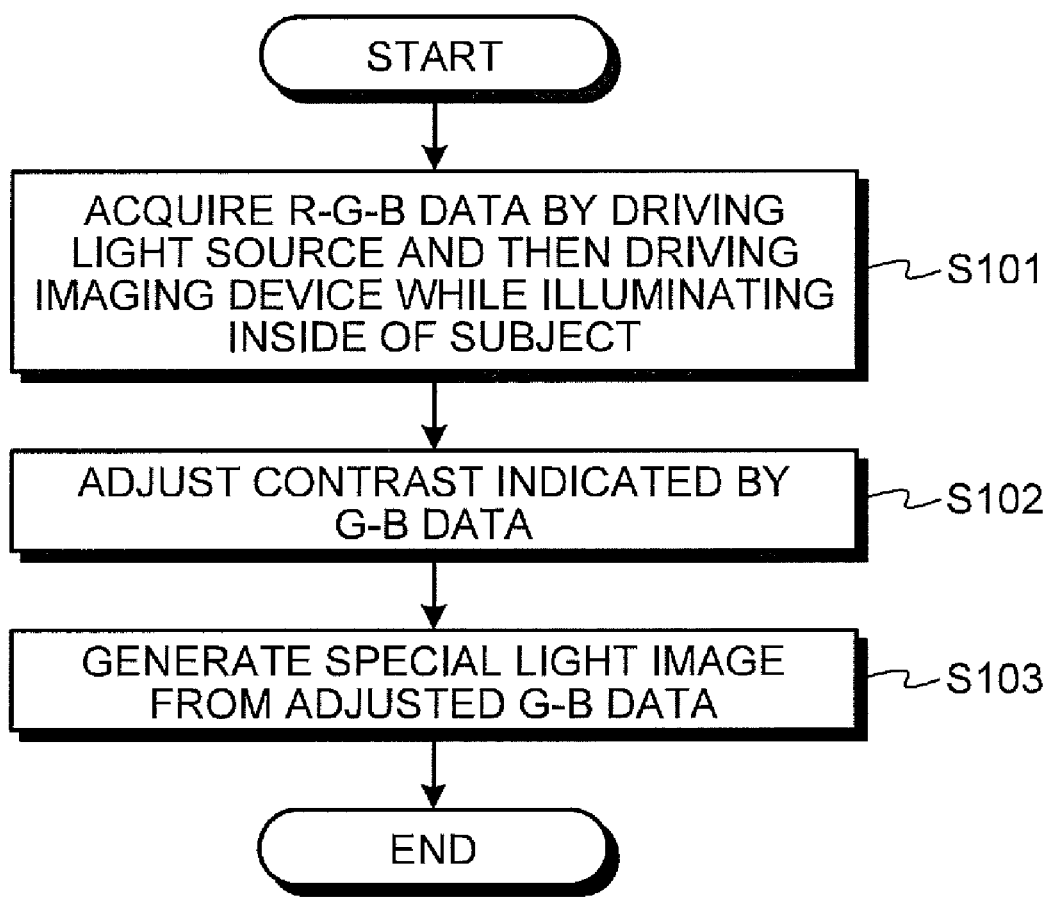
FIG. 11 is a flowchart of an overview of operations for special light observation according to the first embodiment of the present invention.

The operations for special light observation including contrast adjustment for the G data and the B data using the R data will be explained. FIG. 11 is a flowchart of the overview of the operations for special light observation according to the first embodiment.

As FIG. 11 illustrates, in these operations, first, by driving the imaging unit 15A while illuminating the inside of the subject 900 by driving the light source 16A, the capsule medical apparatus 10 acquires the R data, the G data, and the B data (R-G-B) regularly or in response to requests from the user issued via the communication device 130 (step S101).

Subsequently, the contrast indicated by the G data and the B data out of the obtained R-G-B data is adjusted using the R data (step S102). This step S102 may be performed by, for example, the image signal processing circuit 14 in the capsule medical apparatus 10, may be performed by, for example, the received signal processing circuit 134 of the communication device 130, or may be performed by the information processing terminal device 150 that obtains the R-G-B data (image data) via the portable storage medium 140. This step S102 may be performed by analog processing or using digital signals. Furthermore, this step S102 may be performed using an analog/digital circuit or by executing predetermined software.

As described above, after the contrast indicated by the G-B data is adjusted using the R data, a special light image is generated by superimposing any one of the G data and B data, both of which indicate adjusted contrast, on the other (step S103). In this manner, a special light image, in which the blood vessels in the subject 900 are three-dimensionally produced, can be obtained. This step S103 may be performed by the image signal processing circuit 14 of the capsule medical apparatus 10, may be performed by the received signal processing circuit 134 of the communication device 130, or may be performed by the information processing terminal device 150 that obtains the G-B data (image data) after contrast adjustment via the portable storage medium 140. This step S103 may be performed by analog processing or using digital signals. Furthermore, this step S103 may be performed using an analog/digital circuit or by executing predetermined software.

Figure 12:
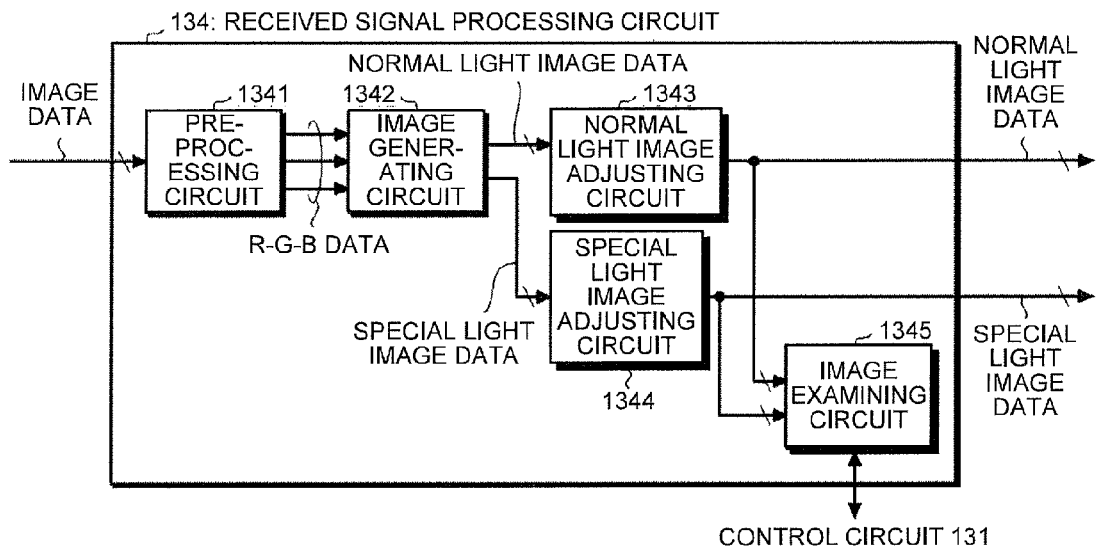
FIG. 12 is a block diagram of a schematic configuration of a received signal processing circuit according to the first embodiment of the present invention.
Figure 13:
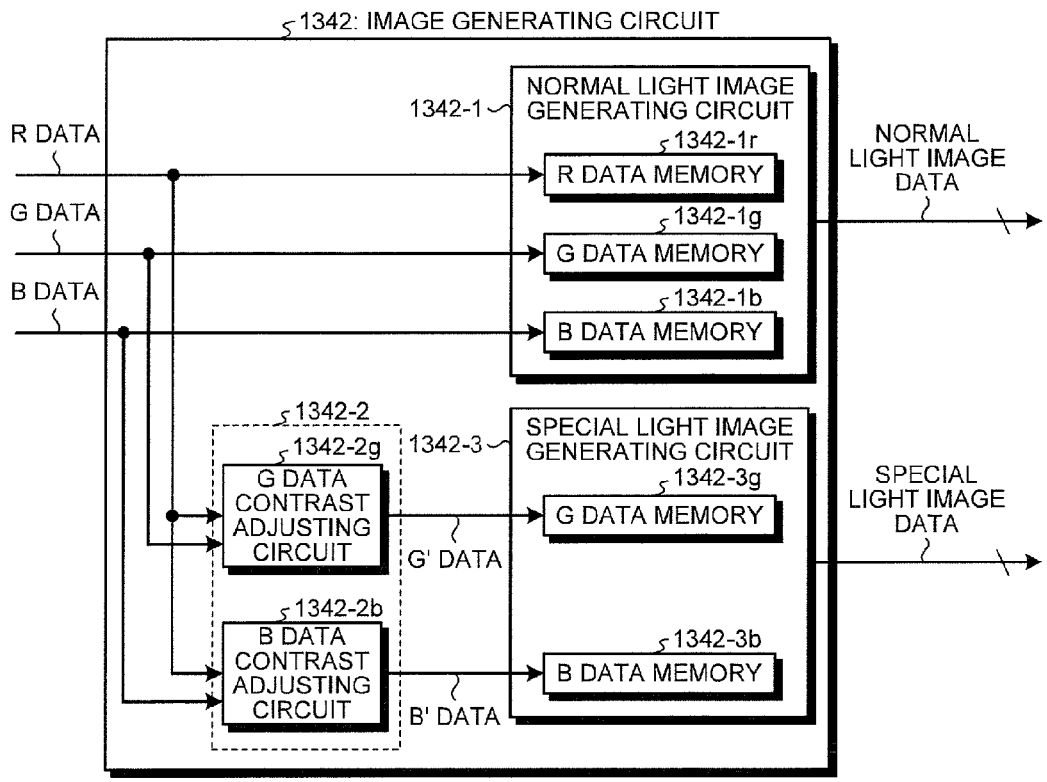
FIG. 13 is a block diagram of a configuration example of an image generating circuit according to the first embodiment of the present invention.

A configuration of the received signal processing circuit 134 of the communication device 130, which is a configuration for performing the processes at step S102 and S103 represented in FIG. 11, will be explained in detail with reference to the drawings. FIG. 12 is a block diagram of a schematic configuration of the received signal processing circuit 134 according to the first embodiment. FIG. 13 is a block diagram of a configuration example of an image generating circuit 1342 represented in FIG. 12. The received signal processing circuit 134 according to the first embodiment is configured to perform special light observation and normal light observation.

As illustrated in FIG. 12, the received signal processing circuit 134 includes a pre-processing circuit 1341 that performs predetermined processes, such as digital to analog conversion (D/A) or separation of color components (R, G, and B components), on image data that is input as digital signals from the capsule medical apparatus 10 via the receiver circuit 133; the image generating circuit 1342 that generates normal light images and special light images, of which contrast is corrected, using the R data, G data, and B data (R-G-B data) that is output from the pre-processing circuit 1341; a normal light image adjusting circuit 1343 that performs processes, such as white balance adjustment, synchronization, color shift, gamma correction, and structure enhancement, on the image data of the normal light images that is output from the image generating circuit 1342 (hereinafter, "normal light image data"); and a special light image adjusting circuit 1344 that performs processes, such as white balance adjustment, synchronization, color shift, gamma correction, and structure enhancement, on the image data of the special light images that is output from the image generating circuit 1342 (hereinafter, "special light image data"). R data, G data, and B data are output from the pre-processing circuit 1341 in synchronization with predetermined horizontal synchronization signals and vertical synchronization signals.

The received signal processing circuit 134 may include an image examining circuit 1345 that determines whether a normal light image, which is generated by the normal light image adjusting circuit 1343, and a special light image, which is generated by the special light image adjusting circuit 1344, are normal. The image examining circuit 1345 detects, for example, the signal level of image data of a normal light image or a special light image, and determines, for example, whether the value is not saturated (saturation). The image examining circuit 1345 inputs the examination result to the control circuit 131. When the normal light image or the special light image is not normal, the control circuit 131 causes each circuit to perform control so that the image is discarded.

As illustrated in FIG. 13, the image generating circuit 1342 represented in FIG. 12 includes a normal light image generating circuit 1342-1 that generates normal light image data from R-G-B data; a G data contrast adjusting circuit 1342-2g that adjusts the contrast indicated by G data on the basis of the R data; a B data contrast adjusting circuit 1342-2b that adjusts the contrast indicated by B data on the basis of the R data; and a special light image generating circuit 1342-3 that generates special light image data from the G data, which indicates the contrast adjusted by the G data contrast adjusting circuit 1342-2g, (hereinafter, "G' data") and the B data, which indicates the contrast adjusted by the B data contrast adjusting circuit 1342-2b (hereinafter, "B' data"). The G data contrast adjusting circuit 1342-2g and the B data contrast adjusting circuit 1342-2b constitute an imaging processor 1342-2 according to the first embodiment.

The normal light image generating circuit 1342-1 includes an R data memory 1342-1r that is a buffer for temporarily storing the R data, a G data memory 1342-1g that is a buffer for temporarily storing the G data, and a B data memory 1342-1b that is a buffer for temporarily storing the B data. The normal light image generating circuit 1342-1 converts the R-G-B data, which is input in analog signals, to digital signals and stores the digital signals in the memories 1342-1r, 1342-1g, and 1342-1b. The normal light image generating circuit 1342-1 generates normal light image data, which contains red (R), green (G), and blue (B) components, by sequentially reading pixel data line by line according to predetermined horizontal synchronization signals and vertical synchronization signals from each memory and by synthesizing the pixel data. The normal light image generating circuit 1342-1 then outputs the normal light image data.

In contrast, the special light image generating circuit 1342-3 includes a G data memory 1342-3g that is a buffer for temporarily storing the G data, which indicates the adjusted contrast, ("G' data") and a B data memory 1342-3b that is a buffer for temporarily storing the B data, which indicates the adjusted contrast, ("B' data"). The special light image generating circuit 1342-3 converts the G'-B' data that is input as analog signals to digital signals and stores the digital signals in the memories 1342-3g and 1342-3b. The special light image generating circuit 1342-3 generates superimposed special light image data containing the green (G) and blue (B) components by sequentially reading pixel data line by line according to predetermined horizontal synchronization signals and vertical synchronization signals from each memory and synthesizing the pixel data. The special light image generating circuit 1342-3 then outputs the special light image data.

In the circuit configuration illustrated in FIG. 13, the G data contrast adjusting circuit 1342-2g and the B data contrast adjusting circuit 1342-2b are circuits for performing the process at step S102 in FIG. 11. The special light image generating circuit 1342-3 is a circuit that performs the process at step S103 in FIG. 11.

Figure 14:
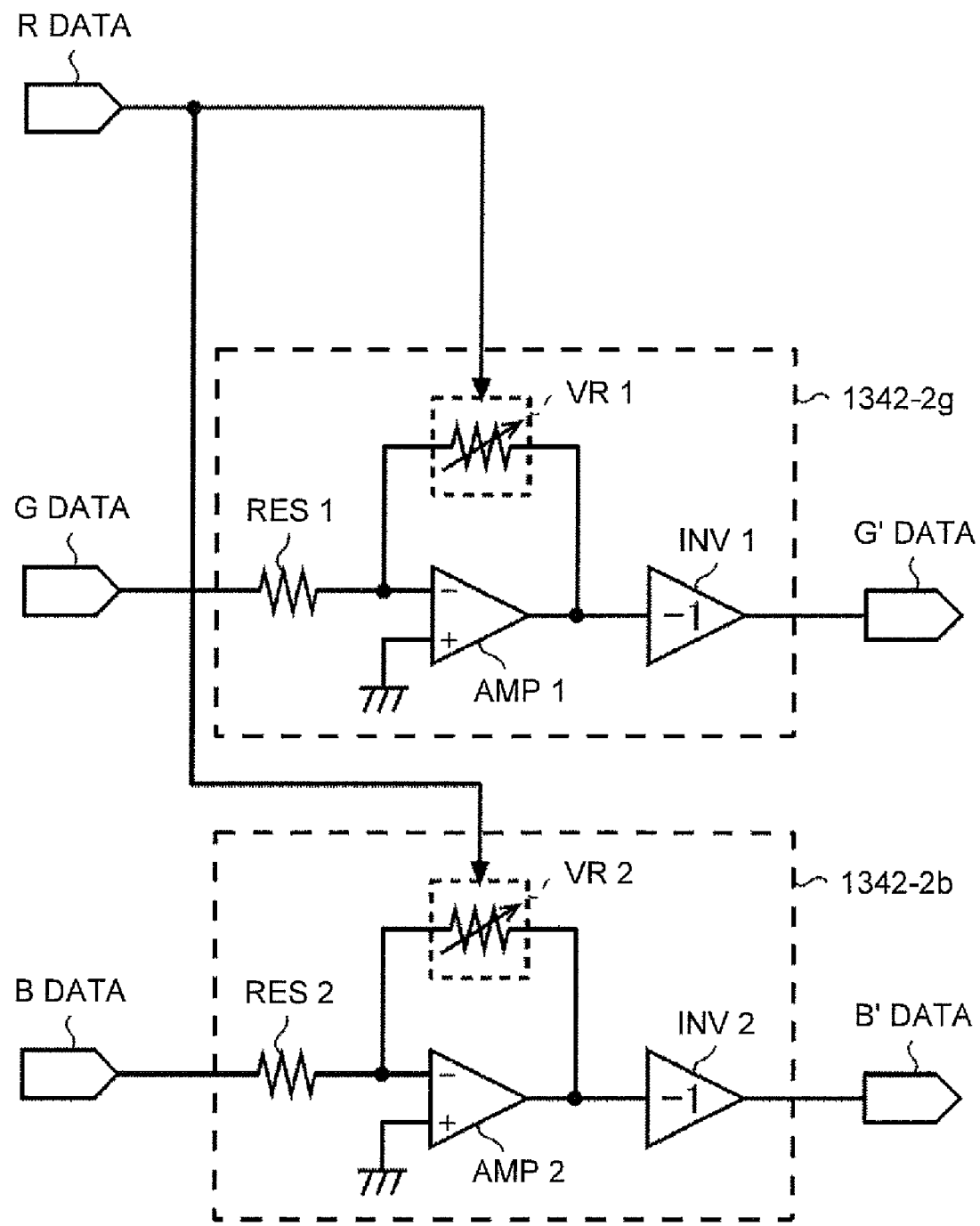
FIG. 14 illustrates a circuit diagram of a circuit configuration example of a G-data contrast adjusting circuit and a circuit diagram of B-data contrast adjusting circuit, with both circuits according to the first embodiment of the present invention.

Circuit configuration examples of the G data contrast adjusting circuit 1342-2g and the B data contrast adjusting circuit 1342-2b that are both represented in FIG. 13 are explained in detail with reference to the drawings. FIG. 14 illustrates a circuit diagram of a circuit configuration example of the G-data contrast adjusting circuit 1342-2g and a circuit diagram of the B data contrast adjusting circuit 1342-2b, with both circuits according to the first embodiment.

As illustrated in FIG. 14, the G data contrast adjusting circuit 1342-2g includes a differential amplifier circuit AMP1, a resistor RES1 that is connected to an inverted input terminal (−) of the differential amplifier circuit AMP1, an inverter INV1 that is provided for the output terminal of the differential amplifier circuit AMP1, and a variable resistor VR1 that is connected between the inverted input terminal (−) and the output terminal of the differential amplifier circuit AMP1. The non-inverted input terminal (+) of the differential amplifier circuit AMP1 is grounded.

In the circuit configuration, the G data out of the R-G-B data, which is output from the pre-processing circuit 1341, is input to the inverted input terminal (−) of the differential amplifier circuit AMP1 via the resistor RES1. The R data is input to a control terminal of the variable resistor VR1. The G data, which is input to the inverted input terminal (−) of the differential amplifier circuit AMP1, and the R data, which is input to the control terminal of the variable resistor VR1, are synchronized according to the predetermined horizontal synchronization signals and the vertical synchronization signals. Because the resistance of the variable resistor VR1 is controlled in accordance with the signal level of the R data, the differential amplifier circuit AMP1 increases the luminance of a unit area represented by the G data in accordance with the luminance of the unit area represented by the R data corresponding to the unit area of the G data.

Using the above circuit configuration, the signal level representing the luminance indicated by the G data, which is input to the inverted input terminal (−) of the differential amplifier circuit AMP1 via the resistor RES1, is amplified according to the following Equation (1) and output as G' data. In Equation (1), G is the signal level representing the luminance indicated by the G data, R is the signal level representing the luminance indicated by the R data, G' is the signal level representing the increased luminance indicated by the G data, and k is an arbitrary constant.

$$G' = G \times (k \times R) \quad (1)$$

Similarly, the B data contrast adjusting circuit 1342-2b includes a differential amplifier circuit AMP2, a resistor RES2 that is connected to an inverted input terminal (−) of the differential amplifier circuit AMP2, an inverter INV2 that is provided for the output terminal of the differential amplifier circuit AMP2, and a variable resistor VR2 that is connected between the inverted input terminal (−) an the output terminal of the differential amplifier circuit AMP2. The non-inverted input terminal (+) of the differential amplifier circuit AMP2 is grounded.

In the circuit configuration, the B data out of the R-G-B data, which is output from the pre-processing circuit 1341, is input to the inverted input terminal (−) of the differential amplifier circuit AMP2 via the resistor RES2. The R data is input to a control terminal of the variable resistor VR2. The B data, which is input to the inverted input terminal (−) of the differential amplifier circuit AMP2, and the R data, which is input to the control terminal of the variable resistor VR2, are synchronized according to the predetermined horizontal synchronization signals and the vertical synchronization signals. Because the resistance of the variable resistor VR2 is controlled in accordance with the signal level of the R data, the differential amplifier circuit AMP2 increases the luminance of a unit area represented by the B data in accordance with the luminance of the unit area represented by the R data corresponding to the unit area represented by the B data.

Using the above circuit configuration, the signal level representing the luminance represented by the B data, which is input to the inverted input terminal (−) of the differential amplifier circuit AMP2 via the resistor RES2, is amplified according to the following Equation (2) and output as B' data. In Equation (2), B is the signal level representing the luminance indicated by the B data, R is the signal level representing the luminance indicated by the R data, B' is the signal level representing the increased luminance indicated by the B data, and k is an arbitrary constant.

$$B' = B \times (k \times R) \quad (2)$$

The G data contrast adjusting circuit 1342-2g and the B data contrast adjusting circuit 1342-2b, which are both illustrated in FIG. 14, are analog circuits that perform analog processing on the R-G-B data. However, the present invention is not limited to this. They may be configured as digital circuits that perform digital processing on the R-G-B data. In this case, digital R-G-B data is used or analog to digital conversion is appropriately performed on the analog R-G-B data and the converted data is used.

As described above, by adjusting the contrast indicated by other data (G-B data in the example) by using data (R data in the example) indicating the highest luminance or data that significantly contains features, such as the shape of an imaging object, the luminance can be increased accurately while reducing noise. Accordingly, accurate contrast adjustment is performed and clear special light images can be generated.

The effects from contrast adjustment according to the first embodiment will be explained in detail with reference to FIG. 15. When a human or an animal is used as the subject 900, as in the first embodiment, the quantity of light of the blue (B) component and the green (G) component that is obtained through illumination by the light source 16A, which outputs white light, is significantly smaller than that of the red (R) component. For this reason, a special light image in the blue (B) component (see, FIG. 15(a)) and a special light image in the green (B) component (see, FIG. 15(b)), which are special light images captured by the imaging unit 15A, which is driven, with illumination by the light source 16A, are very dark and not clear compared with a special light image in the red (R) component (see, FIG. 15(c)). FIGS. 15(a) to 15(c) represent the special light images in the respective components (B, G, and R) that are captured by the imaging unit 15A, which has the spectral sensitivity represented in FIG. 10, while the light source 16A, which has the radiance represented in FIG. 5, illuminates the inside of the subject 900, which has the spectral features of the inner wall in the body cavity and the light absorbance by blood represented in FIGS. 6 and 7.

Figure 15:
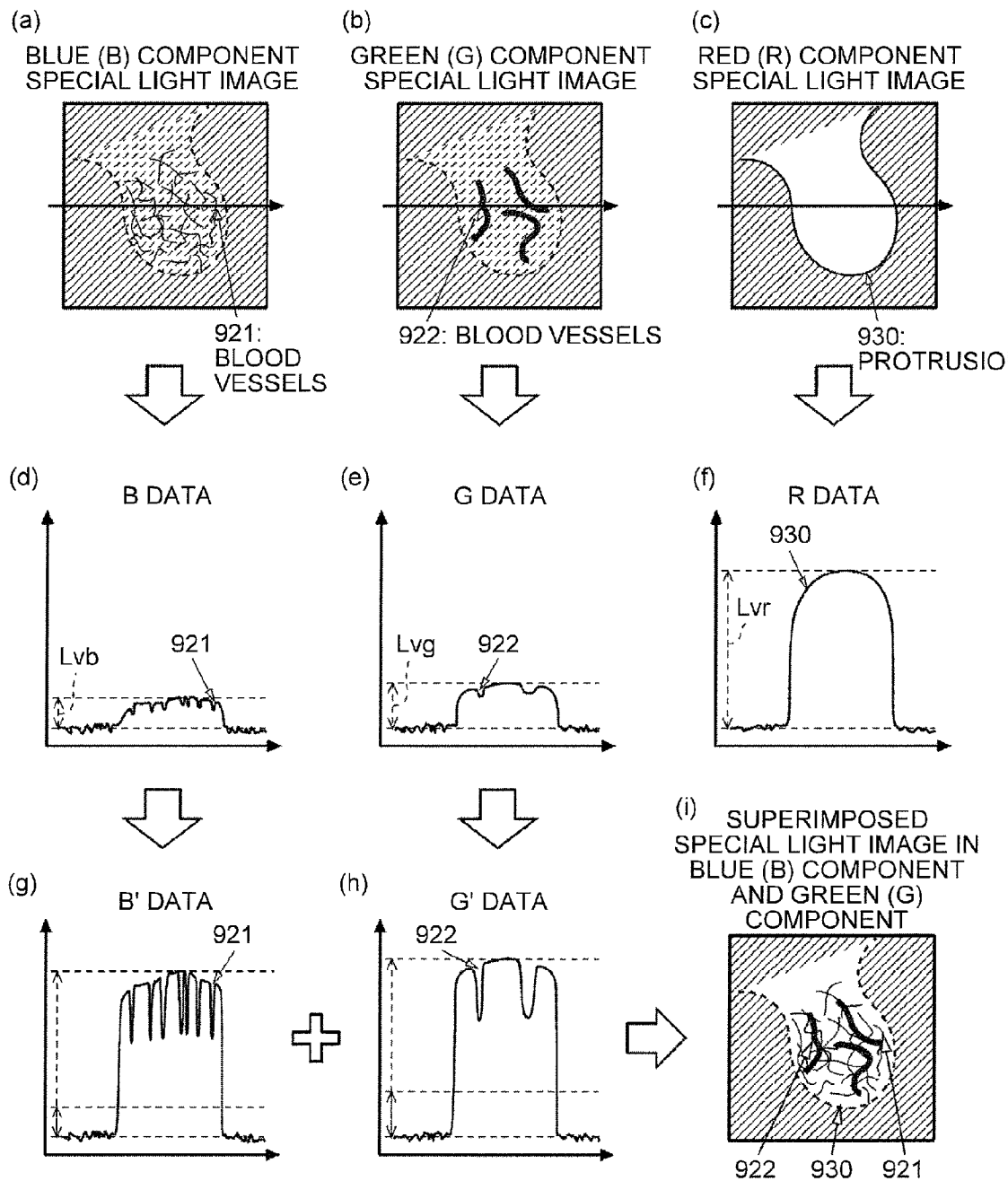
FIG. 15 illustrates diagrams and graphs explaining the effects of contrast adjustments according to the first embodiment of the present invention.

Because the quantity of light of the blue (B) component and the quantity of light of the green component (G) are small, the signal level Lvb of the B data representing the luminance excluding the noise level (see FIG. 15(d)) and the signal level Lvg of the G data representing the luminance excluding the noise level (see FIG. 15(e)) are significantly small compared with the signal level Lvr of the R data representing the luminance excluding the noise level (see FIG. 15(f)). Therefore, variations in the signal level representing the shape of blood vessels, which are variations contained in the B data, (see blood vessels 921 in FIGS. 15(a) and 15(d)) are similar to variations in the signal level resulting from noise. Similarly, variations in the signal level representing the shape of blood vessels contained in the G data (see blood vessels 922 in FIGS. 15(b) and 15(e)) are similar to variations in the signal level resulting from noise. FIG. 15(d) represents the B data of a special light image in the blue (B) component represented in FIG. 15(a), and FIG. 15(e) represents G data of a special light image in the green (G) component represented in FIG. 15(b). FIG. 15(f) represents R data of a special light image in the red (R) component represented in FIG. 15 (c).

As in the first embodiment, by amplifying the B data and the G data, both of which indicate relatively small luminance, by using the R data that indicates high luminance, variations in the signal level representing the shape of the blood vessels contained in the special light image in the blue (B) component (see the blood vessels 921 represented in FIG. 15(g)) and variations in the signal level representing the shape of the blood vessels contained in the special light image in the green (G) component (see the blood vessel 922 represented in FIG. 15(h)) are increased, so the shape contrast can be made clear (see FIG. 15(i)). FIG. 15(g) represents the B' data obtained by amplifying the B data represented in FIG. 15(d) by using the R data represented in FIG. 15(f), and FIG. 15(h) represents the G' data obtained by amplifying the G data represented in FIG. 15(e) by using the R data represented in FIG. 15(f). FIG. 15(i) represents a special light image obtained by superimposing one of a special light image, which is obtained from the B' data represented in FIG. 15(g), and a special light image, which is obtained from the G' data represented in FIG. 15(h), on the other.

In the first embodiment, the R data contains the shape of the imaging object (see protrusion 930 represented in FIGS.

15(c) and 15(f)). For this reason, by amplifying the B data and the G data using the R data, the signal levels of the portions not containing shape features in the B data and the G data, i.e., the portions that contain a lot of noise, are prevented from being increased. Accordingly, clearer special light images can be obtained (see FIG. 15(i)).

In the first embodiment, a human and an animal are taken as examples of the subject 900. However, the present invention is not limited to this. The subject 900 may be changed and various forms may be used, such as a plant or another living organism, or an object that is not a living organism, such as a tank or a pipe. Note that, because the spectral features of the inside of the subject 900 differ depending on the living organism or the object being used as the subject 900, it is preferable that amplification image data that is used to amplify the signal intensity of image data of special light be not limited to R data and be appropriately selected according to the spectral features of the inside of the subject 900. For example, when a plant is used as the subject 900, it is preferable that G data be used for amplification image data because the spectral features of plants have a peak in the green (G) component.

Second Embodiment

A medical system according to a second embodiment of the present invention will be explained in detail below with reference to the drawings. Note that, to simplify the explanations, detailed explanations for configurations similar to those of the first embodiment will be omitted by providing the same reference numerals.

In the first embodiment, the case is exemplified where, by amplifying image data that indicates a relatively low luminance (for example, G-B data) by using image data that indicates the highest luminance (for example, R data) when performing both of normal light observation and special light observation, the contrast in an unclear special light image is enhanced to generate a clear special light image. In contrast, in the second embodiment, a case is exemplified where, by detecting the shape of an imaging object by using image data that notably contains shape features of the imaging object and by amplifying image data, which indicates relatively low luminance, on the basis of the detected shape, the contrast of an unclear special light image is enhanced to generate a clear special light image. The medical system according to the second embodiment has a configuration similar to that of the medical system 1 according to the first embodiment (see FIG. 1). Note that, in the second embodiment, the image generating circuit 1342 according to the first embodiment (see FIG. 13) is replaced with an image generating circuit 2342 (see FIG. 17 described below).

Figure 16:
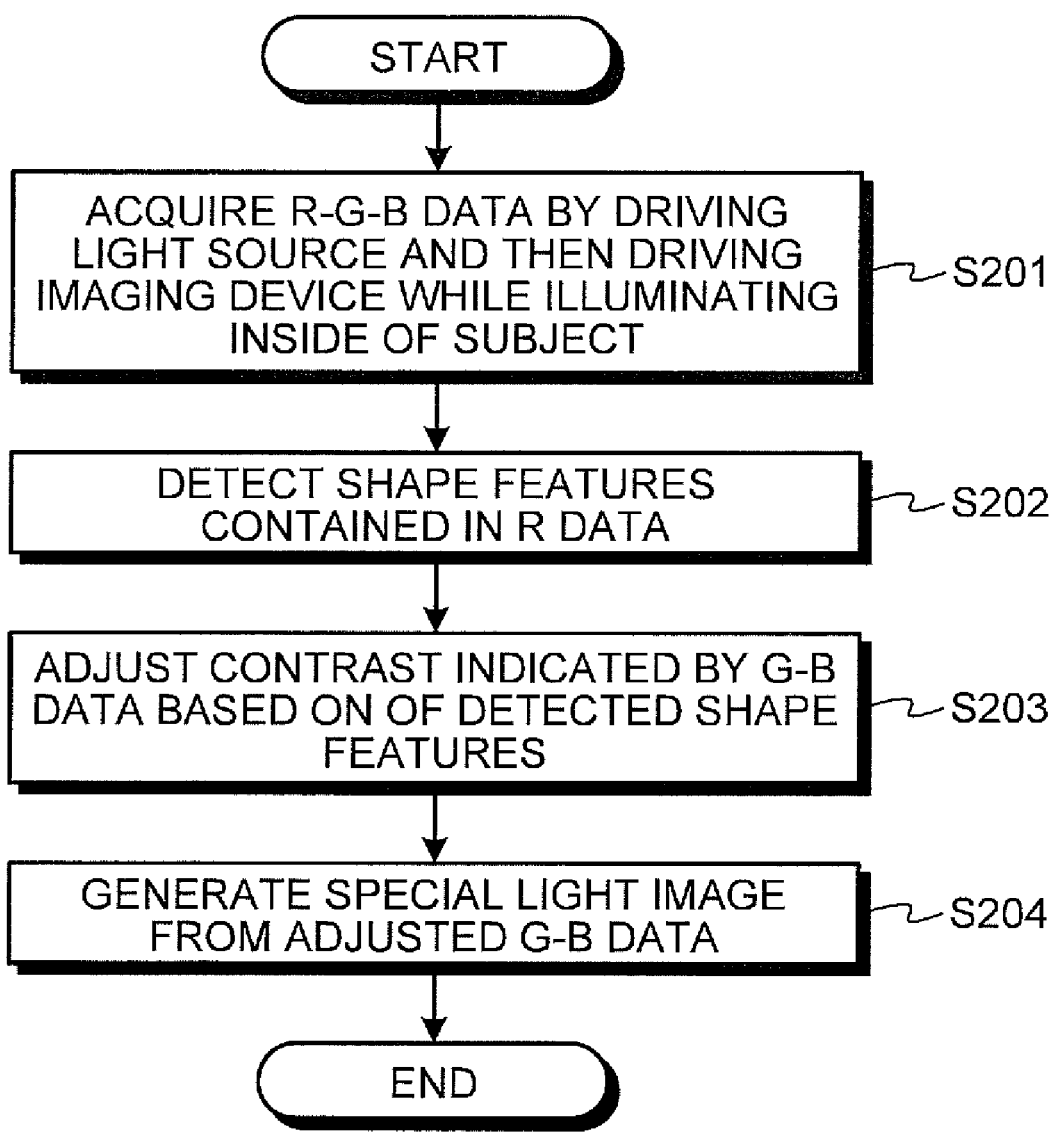
FIG. 16 is a flowchart of an overview of operations for special light observation according to the second embodiment of the present invention.

Operation for special light observation that includes contrast adjustment for G data and B data by using the shape features contained in R data will be explained with reference to FIG. 16. FIG. 16 is a flowchart of an overview of operations for special light observation according to the second embodiment.

As FIG. 16 illustrates, in these operations, first, by driving the imaging unit 15A while illuminating the inside of the subject 900 by driving the light source 16A, the capsule medical apparatus 10 acquires R data, G data, and B data (R-G-B data) regularly or in response to a request from a user issued via the communication device 130 (step S201).

Subsequently, the shape features that are contained in the R data out of the obtained R-G-B data are detected (step S202). This step S202 may be performed by, for example, the image signal processing circuit 14 in the capsule medical apparatus 10, may be performed by, for example, the received signal processing circuit 134 of the communication device 130, or may be performed by the information processing terminal device 150 that obtains the R-G-B data (image data) via the portable storage medium 140. This step S202 may be performed by analog processing or using digital signals. Furthermore, this step S202 may be performed using an analog/digital circuit or by executing predetermined software.

As described above, after the shape features contained in the R data is detected, the contrast indicated by the G data and the B data (G-B data) is adjusted on the basis of the shape features contained in the R data (step S203). For example, by increasing the luminance of an area represented by the G data and the B data, which is an area corresponding to an area to be enhanced, such as a protrusion, on the basis of the shape features detected at step S202, the process at step S203 can be performed. This step S203 may be performed by the image signal processing circuit 14 of the capsule medical apparatus 10, may be performed by the received signal processing circuit 134 of the communication device 130, or may be performed by the information processing terminal device 150 that obtains the R-G-B data (image data) via the portable storage medium 140. This step S203 may be performed by analog processing or using digital signals. Furthermore, this step S203 may be performed using an analog/digital circuit or by executing predetermined software.

As described above, after the contrast indicated by the G-B data is adjusted using the shape features contained in the R data, a special light image is generated by superimposing any one of the G data and the B data, both of which indicate adjusted contrast, on the other (step S204). In this manner, a special light image, in which the blood vessels in the subject 900 are three-dimensionally produced, can be obtained. This step S204 may be performed by the image signal processing circuit 14 of the capsule medical apparatus 10, may be performed by the received signal processing circuit 134 of the communication device 130, or may be performed by the information processing terminal device 150 that obtains the G-B data (image data) after contrast adjustment via the portable storage medium 140. This step S204 may be performed by analog processing or using digital signals. Furthermore, this step S204 may be performed using an analog/digital circuit or by executing predetermined software.

Figure 17:
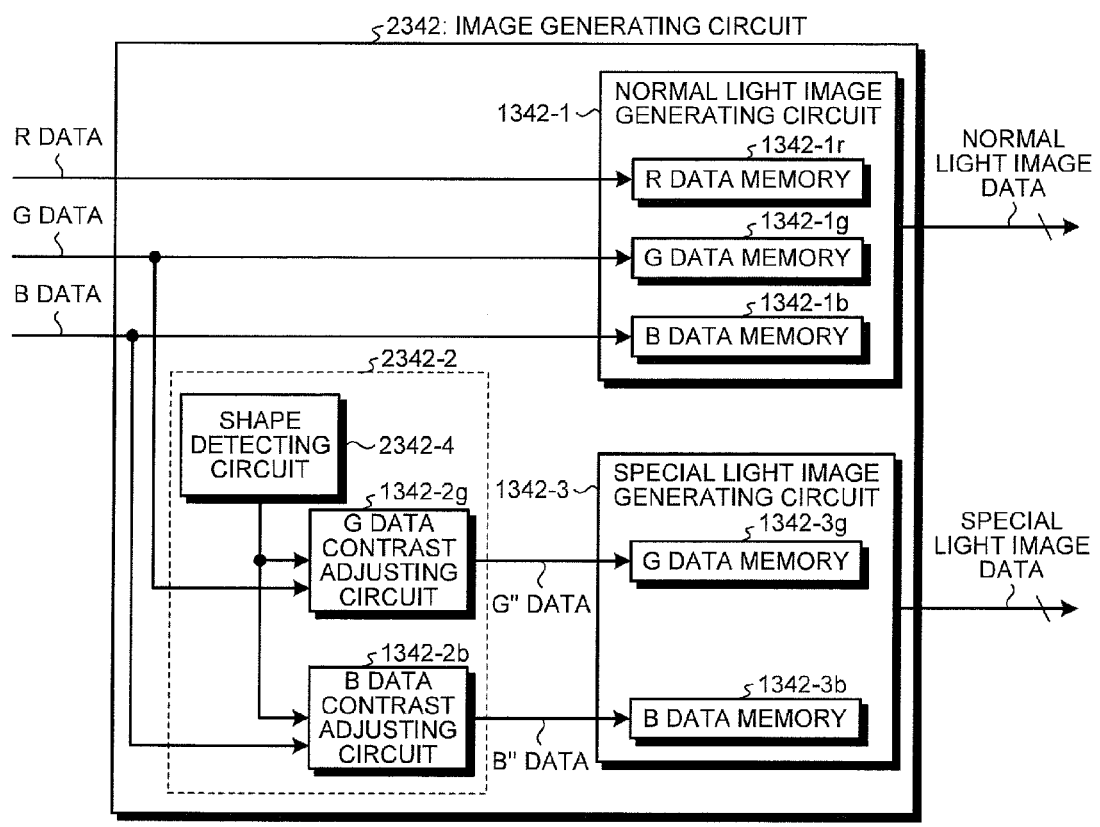
FIG. 17 is a block diagram of a configuration example of an image generating circuit according to the second embodiment of the present invention.

A configuration of the image generating circuit 2342 according to the second embodiment will be explained in detail below. FIG. 17 is a block diagram of a configuration example of the image generating circuit 2342 according to the second embodiment.

As it is clear by comparing FIG. 17 and FIG. 13, the image generating circuit 2342 according to the second embodiment has a configuration similar to that of the image generating circuit 1342 according to the first embodiment. The image generating circuit 2342 has a configuration in which a shape detecting circuit 2342-4 is arranged on an R data input line of the G data contrast adjusting circuit 1342-2g and the B data contrast adjusting circuit 1342-2b. Thus, in the second embodiment, instead of the G data, a detected signal, which is output from the shape detecting circuit 2342-4, is input to each of the G data contrast adjusting circuit 1342-2g and the B data contrast adjusting circuit 1342-2b.

When the luminance indicated by the R data is a pre-set threshold level or higher, the shape detecting circuit 2342-4 outputs a high-level detection signal. When the luminance indicated by the R data is lower than the pre-set threshold level, the shape detecting circuit 2342-4 outputs a low-level detection signal. In other words, the shape detecting circuit 2342-4 outputs a detection signal that synchronizes with the G data and the B data in accordance with the R data. The detection signal is input to the G data contrast adjusting circuit 1342-2g and the B data contrast adjusting circuit 1342-2b.

When the detection signal that is input from the shape detecting circuit 2342-4 is a high-level signal, the G data contrast adjusting circuit 1342-2g amplifies the G data in accordance with a predetermined gain and outputs the data as G" data. Similarly, when the detection signal, which is input from the shape detecting circuit 2342-4, is a high-level signal, the B data contrast adjusting circuit 1342-2b amplifies the B data according to a predetermined gain and outputs the data as B" data. The shape detecting circuit 2342-4, the G data contrast adjusting circuit 1342-2g, and the B data contrast adjusting circuit 1342-2b constitute an imaging processor 2342-2 according to the second embodiment.

Figure 18:
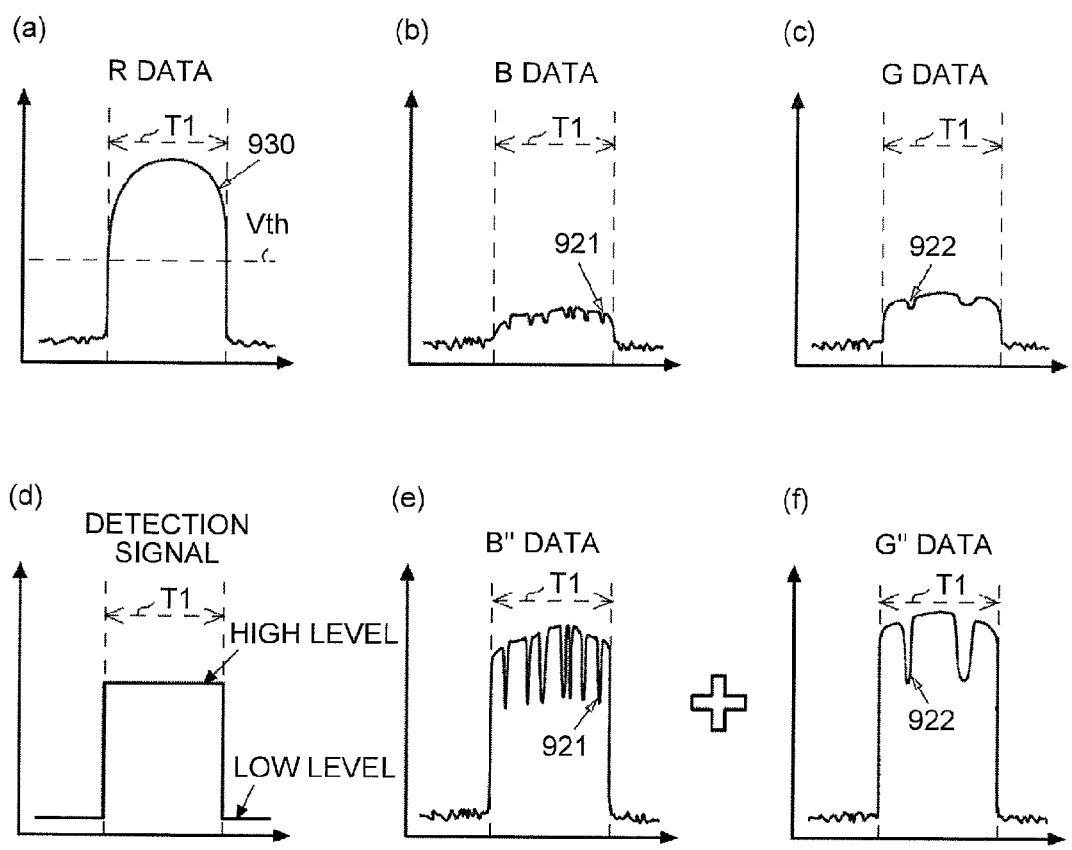
FIG. 18 illustrates graphs for explaining the effects of contrast adjustment according to the second embodiment of the present invention.

In other words, in the example illustrated in FIG. 18, when the luminance indicated by the R data, which is represented in (a) is at a threshold level Vth or higher, the shape detecting circuit 2342-4 outputs a high-level detection signal as illustrated in (d). The high-level detection signals are output for a period T1 in which the luminance indicated by the R data is at a threshold level Vth or higher. In a period in which the luminance indicated by the R data is lower than the threshold level Vth, the shape detecting circuit 2342-4 outputs low-level detection signals. Because the B data contrast adjusting circuit 1342-2b increases the luminance indicated by the B data, which is represented in (b), in accordance with the signal level of the detection signal, which is output from the shape detecting circuit 2342-4, the B data contrast adjusting circuit 1342-2b outputs the B" data indicating the increased luminance in the period T1 as illustrated in (e). Similarly, because the G data contrast adjusting circuit 1342-2g increases the luminance indicated by the G data, which is represented in (c), in accordance with the signal level of the detection signal, which is output from the shape detecting circuit 2342-4, the G data contrast adjusting circuit 1342-2g outputs the G" data indicating the increased the luminance in the period T1 as illustrated in (f). FIG. 18 illustrates graphs for explaining the effects of the contrast adjustment according to the second embodiment. FIGS. 18(a), 18(b), and 18(c) correspond respectively to FIGS. 15(a), 15(b), and 15(c).

The D" data and the B" data that are output respectively from the G data contrast adjusting circuit 1342-2g and the B data contrast adjusting circuit 1342-2b and are input to the special light image generating circuit 1342-3 as in the first embodiment of the present invention. Thereafter, a superimposed special light image data that contains the green (G) and blue (B) components, is generated appropriately and is output.

As described above, in the second embodiment, by adjusting the contrast indicated by other data (G-B data in the example) by using data (R data in the example) that notably contains the shape features of an imaging object, the luminance can be increased accurately while reducing noise as in the first embodiment of the present invention.

Accordingly, accurate contrast adjustment is performed and clear special light images can be generated.

Modifications

In the first and second embodiments, the configuration is exemplified where, when the luminance indicated by image data in a reference color component (the R data in this example) represents a predetermined threshold or larger, image data in other color components (the G-B data in this example) is amplified to increase the luminance indicated by special light image data is on the basis of the shape of an imaging object. However, the present invention is not limited to this. Various modifications can be made. For example, a configuration can be taken in which edge determining process is performed on image data in a reference color component to specify the shape of an imaging object and the luminance indicated by special light image data is increased on the basis of the specified shape. The shape may be specified two-dimensionally or three-dimensionally. When it is determined three-dimensionally, it is preferable to change the amplification factor according to the variations in the shape.

According to the first and second embodiments, the contrast of an image can be adjusted for each wavelength component using a simple configuration in which the luminance indicated by other image data is increased on the basis of the luminance of a piece of image data. Accordingly, a clear image in each wavelength component can be generated using a compact and simple configuration.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An imaging processor comprising:
    an amplifier that increases a luminance indicated by green and blue image data on the basis of a luminance indicated by red image data out of a plurality of pieces of image data in respective wavelength components, which are pieces of image data representing a same area,
    wherein the amplifier increases a luminance of a unit area represented by the green and blue image data on the basis of a luminance in an area corresponding to the unit area represented by the red image data.

2. The imaging processor according to claim 1, wherein the amplifier includes
    a differential amplifier circuit that includes an inverted input terminal, to which the green and blue image data is input, and a non-inverted input terminal that is grounded;
    a variable resistor that includes a control terminal to which the red image data is input in synchronization with the green and blue image data, and that is connected between the inverted input terminal and an output terminal of the differential amplifier circuit; and
    an inverter circuit that is connected to the output terminal of the differential amplifier circuit.

3. An imaging processor comprising:
    an amplifier that increases a luminance indicated by green and blue image data on the basis of a luminance indicated by red image data out of a plurality of pieces of image data in respective wavelength components, which are pieces of image data representing a same area, wherein
    the amplifier includes a shape detector that detects a shape that is contained in the red image data on the basis of the luminance indicated by the red image data, and
    the amplifier increases the luminance indicated by the green and blue image data on the basis of the shape that is detected by the shape detector.

4. The imaging processor according to claim 3, wherein the amplifier includes
    a differential amplifier circuit that includes an inverted input terminal, to which the green and blue image data is input, and a non-inverted input terminal that is grounded;

a variable resistor that includes a control terminal to which the red image data is input in synchronization with the green and blue image data, and that is connected between the inverted input terminal and an output terminal of the differential amplifier circuit; and an inverter circuit that is connected to the output terminal of the differential amplifier circuit.

5. The imaging processor according to claim 3, wherein the shape detector detects whether the red image data is input to the shape detector and the luminance indicated by the red image data is a predetermined value or higher, and outputs a result of the detection as a detection signal, and the amplifier includes a differential amplifier circuit that includes an inverted input terminal, to which the green and blue image data is input in synchronization with the red image data, and a non-inverted input terminal that is grounded;

a variable resistor that includes a control terminal to which the detection signal output from the shape detector is input, and that is connected between the inverted input terminal and an output terminal of the differential amplifier circuit; and an inverter circuit that is connected to the output terminal of the differential amplifier circuit.

6. An image processing method comprising:

an amplifying step of increasing luminance indicated by green and blue image data on the basis of luminance indicated by red image data out of a plurality of pieces of image data in respective wavelength components, which are pieces of image data representing the same area, wherein the amplifying step includes increasing a luminance of a unit area represented by green and blue image data on the basis of a luminance in an area corresponding to the unit area represented by the red image data.

7. An image processing method comprising:

an amplifying step of increasing a luminance indicated by image data in a wavelength component other than a specific wavelength component on the basis of a luminance indicated by the image data in the specific wavelength component out of a plurality of pieces of image data in respective wavelength components, which are pieces of image data representing a same area; and a shape detecting step of detecting a shape that is contained by the red image data on the basis of the luminance indicated by the red image data, wherein the amplifying step includes increasing the luminance indicated by the green and blue image data on the basis of the shape that is detected at the shape detecting step.

* * * * *